United States Patent
Jenkins et al.

(10) Patent No.: US 8,518,888 B2
(45) Date of Patent: Aug. 27, 2013

(54) METHOD OF TREATMENT OF GASTROINTESTINAL-TYPE CANCER WITH ANTAGONISTIC ANTIBODIES TO IL-11R

(75) Inventors: Brendan J. Jenkins, Viewbank (AU); Tracy Lynn Putoczki, North Melbourne (AU); Matthias Ernst, Brunswick West (AU); Andrew Jarnicki, Brunswick (AU); Brent McKenzie, Sunshine (AU)

(73) Assignees: CSL Limited, Parkville, Victoria (AU); Ludwig Institute for Cancer Research Ltd., New York, NY (US)

( * ) Notice: Subject to any disclaimer, the term of this patent is extended or adjusted under 35 U.S.C. 154(b) by 110 days.

(21) Appl. No.: 12/578,946

(22) Filed: Oct. 14, 2009

(65) Prior Publication Data
US 2010/0183544 A1    Jul. 22, 2010

Related U.S. Application Data

(60) Provisional application No. 61/105,179, filed on Oct. 14, 2008.

(51) Int. Cl.
*A61K 39/00* (2006.01)
*A61K 35/00* (2006.01)
*A61K 39/395* (2006.01)
*C07K 16/28* (2006.01)

(52) U.S. Cl.
USPC .............. 514/19.3; 424/130.1; 424/139.1; 530/387.1; 530/389.1

(58) Field of Classification Search
None
See application file for complete search history.

(56) References Cited

U.S. PATENT DOCUMENTS

| | | | |
|---|---|---|---|
| 6,274,547 B1 * | 8/2001 | Tobin | 514/21.2 |
| 2004/0142871 A1 * | 7/2004 | Shaughnessy et al. | 514/12 |
| 2007/0190024 A1 * | 8/2007 | Paris et al. | 424/85.2 |

OTHER PUBLICATIONS

Wang et al., Nature Medicine 8(10)1080-1082, 2002.*
Kuenzler et al., IL-11 pretreatment reduces cell death after intestinal ischemia—reperfusion, J. Surgical Res., 108, 268-272, 2002.*
Cheng et al., Crossreactivity of antibody against SARS-coronavirus nucleocapsid protein with IL-11, Biochem. Biophys. Res. Commun. 338, 1654-1660, 2005.*
Potten CS, Protection of the small intestinal clonogenic stem cells from radiation-induced damage by pretreatment with interleukin also increases murine survival time, Stem Cells (Dayt.), 14, 452-459, 1996.*
Yoshizaki et al., Expression of interleukin IL-11 and IL-11 receptor in human colorectal adenocarcinoma: IL-11 up-regulation of the invasive and proliferative activity of human colorectal carcinoma cells, Int. J. Oncol., 29, 869-876, 2006.*
Ernst et al., STAT3 and STAT1 mediate IL-11—dependent and inflammation-associated gastric tumorigenesis in gp130 receptor mutant mice, J. Clin. Investig. 118, 1727-1738, 2008.*
Fasnacht N., et al., "Conditional gp130 deficient mouse mutants", Seminars in Cell & Developmental Biology, 19:379-384 (2008).
Tebbutt N. C. et al., "Reciprocal regulation of gastrointestinal homeostasis by SHP2 and STAT-mediated trefoil gene activation in gp 130 mutant mice", Nature Medicine, 8(10):1089-1097 (Oct. 2002).

* cited by examiner

*Primary Examiner* — Elly-Gerald Stoica
(74) *Attorney, Agent, or Firm* — Scully, Scott, Murphy & Presser, P.C.

(57) ABSTRACT

The present invention relates generally to the field of cancer therapy. More particularly, the present invention provides a method for the treatment of gastrointestinal-type cancers and therapeutic agents useful for same.

6 Claims, No Drawings

METHOD OF TREATMENT OF GASTROINTESTINAL-TYPE CANCER WITH ANTAGONISTIC ANTIBODIES TO IL-11R

CROSS-REFERENCE TO RELATED APPLICATIONS

This application claims the benefit of U.S. Provisional Application No. 61/105,179 filed on Oct. 14, 2008.

FIELD

The present invention relates generally to the field of cancer therapy. More particularly, the present invention provides a method for the treatment of gastrointestinal-type cancers and therapeutic agents useful for same.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Gastrointestinal-type cancers are malignant conditions which occur in the gastrointestinal tract including the stomach, oesophagus, liver, biliary system, pancreas, bowels and anus. Cancer of the stomach, generally referred to as gastric cancer (GC), is the second most common cause of cancer-related deaths worldwide (Parkin et al, *CA Cancer J Clin* 55:74-108, 2005). The high mortality and morbidity rate of GC highlights the need and imperative to develop effective treatments.

Although the molecular mechanisms underlying the pathogenesis of GC remain to be fully defined, a causal correlation has been established between GC and chronic inflammation triggered by the Gram-negative bacterium, *Helicobacter pylori* (Uemura et al, *N Engl J Med* 345:784-789, 2001) which colonizes the epithelium of the gastric mucosa. Several genetic factors have also been linked to GC, including accumulation of (epi-) genetic alterations in p53 (Wang et al, *Anticancer Res.* 21:513-520, 2001), tff1 (Park et al, *Gastroenterology* 119:691-698, 2000), E-cadherin (Guilford et al, *Nat Med* 392:402-405, 1998), Cox2 (Rocco et al, *Annals of Oncology* 17:103-108, 2006) as well as genes encoding components of the transforming growth factor (TGF)-β/Smad signaling cascade (Takaku et al, *Cancer Res.* 59:6113-6117, 1999; Xu et al, *Oncogene* 19:1868-1874, 2000; Massague et al, *Cell* 103:295-309, 2000; Boivin et al, *Lab Invest.* 74:513-518, 1996). Persistent activation of the latent signal transducer and activator of transcription (STAT) 3 has been proposed as a prognostic factor for poor survival of GC patients (Gong et al, *Clin Cancer Res.* 11:1386-1393, 2005), while excessive STAT3 activation promotes the growth and survival of gastric cells (Kanda et al, *Oncogene* 23:4921-4929, 2004; Kanai et al, *Oncogene* 22:548-554, 2003) and is associated with increased gastric angiogenesis (Gong et al, 2005 supra).

Interleukin (IL)-11 (IL-11) is a member of the IL-6 cytokine family which also comprises IL-27, IL-31, leukemia inhibitory factor (LIF), oncostatin M (OSM) and ciliary neurotrophic factor (CNTF) amongst others, and plays a crucial role in hematopoiesis, the immune response and inflammation (Becker et al, *Cell Cycle* 4:217-220, 2005; Naugler et al, *Science* 317:121-124, 2007; Kishimoto et al, *Blood* 86:1243-1254, 1995). IL-6 family cytokines execute their actions via the common signal-transducing receptor β-subunit, gp130. In particular, binding of IL-6 or IL-11 to their specific receptor α-subunits, IL-6Rα and IL-11Rα, respectively, induces gp130 homodimerization, while other family members engage heterodimeric receptor complexes comprising gp130 and either the LIF-receptor (R), OSM-R or WSX-1 β-subunits (Heinrich et al, *Biochem J.* 374:1-20, 2003). Ligand-induced β-subunit dimerization subsequently activates receptor-associated Janus kinases (Jak), leading to phosphorylation of cytoplasmic Y residues (Heinrich et al, *Biochem J* 334(Pt 2):297-314, 1998). Phosphorylation of the four carboxy-terminal Y residues in gp130 is required and sufficient for the activation of STAT3 and to a lesser extent of STAT1 (Gerhartz et al, *J. Biol. Chem.* 271:12991-12998, 1996). Meanwhile, the membrane-proximal phosphorylated Y residue in gp130 ($pY_{757}$ in mouse, $pY_{759}$ in human) provides a binding site for the tyrosine phosphatase Shp2 (Nicholson et al, *Proc Natl Acad Sci USA* 97:6493-6498, 2000), which upon phosphorylation mediates activation of the Ras/Erk and PI3K/Akt pathways (Takahashi-Tezuka et al, *Mol Cell Biol.* 18:4109-4117, 1998).

STAT3 induces expression of genes associated with angiogenesis (e.g. VEGF), cell cycle progression (e.g. cylin D1) and cell survival (e.g. Bcl-XL, survival) [Jenkins et al, *Nat Med* 11:845-852, 2005]. Furthermore, persistent STAT3 activity appears to be associated with hematologic malignancies and tumors of epithelial origin (Gong et al, 2005 supra; Kanda et al, 2004 supra; Jenkins et al, 2005 supra; Levy and Lee, *J Clin Invest* 109:1143-1148, 2002).

De-regulated activation of the latent STAT3 is associated with a number of hematological and epithelial malignancies, including GC. Whilst exaggerated STAT3 and/or STAT1 signaling facilitates an anti-apoptotic, pro-angiogenic and pro-proliferative environment for neoplastic cells, the molecular mechanisms leading to STAT3 and/or STAT1 hyperactivation have been poorly understood.

There is a need to develop therapies for gastrointestinal-type cancers and in particular GC and colorectal cancer.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

Singular forms "a", "an" and "the" include plural aspects unless the context clearly dictates otherwise. Thus, for example, reference to "a cytokine" includes a single cytokine, as well as two or more cytokines; reference to "an antibody" includes a single antibody, as well as two or more antibodies; reference to "the invention" includes a single and multiple aspects of an invention; and so forth.

In accordance with the present invention, it is determined that interleukin (IL)-11 promotes chronic gastric inflammation and associated tumorigenesis in an animal model comprising $gp130^{Y757F/Y757F}$ mice where the mutated gp130 signaling receptor subunit cannot bind the negative regulator suppressor of cytokine signaling $(SOCS)_3$ that is characterized by STAT3 and STAT1 hyperactivation. Surprisingly, in gp130$^{Y757F/Y757F}$; IL-11Rα$^{-/-}$ mice (i.e. gp130$^{Y757F/Y757F}$ mice lacking the IL-11 ligand-binding receptor subunit) there was complete absence of gastric disease and this coincided with normalized gastric STAT3 activation and IL-11 expression. Furthermore, treatment of gp130$^{Y757F/Y757F}$ mice with an antagonist of IL-11 or IL-11R also reduced gastric tumorigenesis. Collectively, the data identify IL-11 as a crucial cytokine promoting chronic gastric inflammation and associated tumorigenesis, and show that inhibition of IL-11 signalling may reduce chronic gastric inflammation and associated tumorigenesis. Furthermore, gp130$^{Y757F/Y757F}$ IL-11Rα$^{-/-}$ mice were also resistant to the development of cancer in an animal model of colorectal cancer.

In accordance with the present invention, it is proposed that the growth and maintenance of gastrointestinal-type cancers such as GC or colorectal cancer are inhibited or otherwise arrested by antagonizing IL-11 or IL-11-mediated signaling (such as via its receptor, IL-11R).

Hence, the present invention is directed to the use of antagonists of IL-11 and/or IL-11 receptor (IL-11R) in the treatment of gastrointestinal-type cancers. Such conditions include malignant conditions in the stomach, liver, biliary system, pancreas, bowels and anus. In particular, the present invention provides the use of antagonists of IL-11 and/or IL-11R in the treatment of GC or colorectal cancer.

The term "GC" includes stomach cancer and associated cancers and conditions. The term "treatment" includes amelioration of symptoms and delaying onset of symptoms as occurs with prophylaxis. The present invention is predicated in part on the elucidation of the role of IL-11 in the persistent activation of STATs and the effects of an antagonist of IL-11 or IL-11R in an animal model. In accordance with the present invention, therefore, inhibiting the activity of IL-11 or IL-11-mediated signaling is proposed to be useful in the treatment of gastrointestinal-type cancers such as GC or colorectal cancer.

Accordingly, one aspect of the present invention contemplates a method for the treatment of a gastrointestinal cancer in a subject, the method comprising administering to the subject an antagonist of IL-11 or IL-11R. The antagonist is provided in an effective amount. Reference to an "effective amount" is an amount sufficient to ameliorate the symptoms of the gastrointestinal-type cancer and/or delay onset of conditions surrounding or associated with the cancer. The administration is generally for a time and under conditions sufficient to ameliorate all or at least some of the symptoms including reducing gastric tumor burden. In addition, the effective amount may also be considered in terms of the amount required to down-regulate levels of a STAT such as STAT3 and/or STAT1. Furthermore, the amount is generally effective to inhibit IL-11-mediated signaling.

In a particular embodiment, the gastrointestinal-type cancer is gastric cancer (GC).

In another embodiment, gastrointestinal-type cancer is colorectal cancer.

Hence, the present invention provides a method for the treatment of GC in a subject, the method comprising administering to the subject an antagonist of IL-11 or IL-11R.

The present invention also provides a method for the treatment of colorectal cancer in a subject, the method comprising administering to the subject an antagonist of IL-11 or IL-11R.

Particular antagonists of IL-11 or IL-11R include an IL-11 mutein, an anti-IL-11 antibody, an anti-IL11R antibody and a soluble IL-11R. An "antagonist of IL-11 or IL-11R" may also be a agent which inhibits expression of genes encoding IL-11 and/or IL-11R.

As indicated above, the agent is generally administered in an amount and for a time and under conditions sufficient to ameliorate the symptoms of the gastrointestinal-type cancer and this includes reducing gastric tumor burden. In a particular embodiment, the symptoms ameliorated are those in respect of the colorectal cancer.

The administration may be systemic or local. Systemic administration is particularly useful. Reference to "systemic administration" includes intra-artery, intravenous, intraperitoneal and subcutaneous injection, infusion, as well as administration via oral, rectal and nasal routes, or via inhalation.

The present invention further contemplates combination therapy such as targeting IL-11 and/or IL-11R signaling and providing one or more anti-cancer agents and/or adopting therapeutic protocols such as chemotherapy, radiation therapy or surgical ablation of cancer tissue.

Accordingly, another aspect of the present invention relates to a method for the treatment of a gastrointestinal-type cancer in a subject, the method comprising administering an antagonist of IL-11 or IL-11R together with at least one other therapeutic agent and/or in association with a procedure selected from chemotherapy, radiation therapy and surgical ablation of cancer tissue.

Another aspect of the present invention relates to a method for the treatment of a GC in a subject, the method comprising administering an antagonist of IL-11 or IL-11R together with at least one other therapeutic agent and/or in association with a procedure selected from chemotherapy, radiation therapy and surgical ablation of cancer tissue.

A further aspect of the present invention provides a method for the treatment of colorectal cancer in a subject, the method comprising administering an antagonist of IL-11 or IL-11R together with at least one other therapeutic agent and/or in association with a procedure selected from chemotherapy, radiation therapy and surgical ablation of cancer tissue.

Reference to "together with" includes sequential or simultaneous treatments.

Particular subjects are mammals such as humans.

The present invention extends to the use of pharmaceutical compositions comprising antagonists of IL-11 and/or IL-11R. Useful compositions include those comprising an IL-11 mutein, an anti-IL-11 antibody, an anti-IL-11R antibody, or a soluble IL-11R.

The present invention further contemplates the use of an antagonist of IL-11 or IL-11R in the manufacture of a medicament for the treatment of a gastrointestinal-type cancer.

The present invention also provides for the use of an antagonist of IL-11 or IL-11R in the manufacture of a medicament for the treatment of GC in a subject.

The present invention further provides for the use of an antagonist of IL-11 or IL-11R in the manufacture of a medicament for the treatment of colorectal cancer in a subject.

A medical kit is also provided comprising an antagonist of IL-11 or IL-11R together with instructions to use the antagonists in the treatment of a gastrointestinal-type cancer such as GC or colorectal cancer.

The present invention further provides a therapeutic protocol for treating GC in a subject, the protocol comprising screening a biopsy of gastric tissue for expression levels of IL-11 and, in subjects having tissue with high IL-11 expression levels, providing an IL-11 or IL-11R antagonist for a time and under conditions to reduce potential tumorigenesis and/or to ameliorate gastric tumor burden.

The present invention is also directed to a therapeutic protocol for treating colorectal cancer in a subject, the protocol comprising screening a biopsy of colorectal tissue for expression levels of IL-11 and, in subjects having tissue with high IL-11 expression levels, providing an IL-11 or IL-11R antagonist for a time and under conditions to reduce potential tumorigenesis and/or to ameliorate colorectal tumor burden.

TABLE 1

Summary of sequence identifiers

| SEQUENCE ID NO: | DESCRIPTION |
|---|---|
| 1 | Amino acid sequence of murine IL-11 mutein |
| 2 | Amino acid sequence of murine IL-11 mutein |
| 3 | Amino acid sequence of murine IL-11 mutein |
| 4 | Amino acid sequence of human IL-11 mutein |

Abbreviations and terms used in the present specification are defined in Table 2.

TABLE 2

Abbreviations

| Abbreviation | Definition |
|---|---|
| CNTF | Ciliary neurotrophic factor |
| F | Phenylalanine |
| Gastrointestinal-type cancer | A cancer of the stomach, oesophagus, liver, biliary system, pancreas, bowels or anus. Includes GC and colorectal cancer. Also refers to as "gastrointestinal cancer". |
| GC | Gastric cancer |
| gp130 | Common signal-transducing receptor β-subunit |
| gp130$^{+/+}$ | Mice with wild-type gp130 gene |
| gp$^{Y757F/Y757F}$ mice | Homozygous knock-in substitution mutation from tyrosine to phenylalanine at residue 757 of gp130 which abolishes a negative feedback mechanism to terminate gp130 signaling |
| Jak | Janus kinase |
| LIF | Leukemia Inhibitory Factor |
| OSM | Oncostatin M |
| PEG | Polyethyleneglycol |
| PEGylated | Polyethyleneglycosylated |
| PEGylation | Polyethyleneglycosylation |
| SOCS | Suppressor of cytokine signaling |
| STAT | Signal transducer and activator of transcription |
| Y | Tyrosine |

DETAILED DESCRIPTION

The present invention is predicated in part on an elucidation of the role of IL-11 in STAT3 and STAT1 activation using an animal model, the gp130$^{Y757F/Y757F}$ mouse. This mouse model is described in Jenkins et al, 2005 supra; Jenkins et al, *Blood* 109:2380-2388, 2007; Howlett et al, *Gastroenterology* 129:1005-1018, 2005.

The gp130$^{Y757F/Y757F}$ mouse is a validated, reproducible and genetically defined model for gastric tumorigenesis and shares many of the histological hallmarks of inflammation-associated intestinal-type GC in humans. This model is now extended to be an informative preclinical disease model which provides definitive genetic proof for IL-11's pivotal role in mediating aberrant STAT3 and STAT1 activation. In turn, aberrant activation of these latent transcription factors promotes atrophic gastritis that culminates in dysplastic and frequently metaplastic epithelial transformation and the outgrowth of distinct adenomatous polyps. Furthermore, it provides an endogenous tumor model for therapeutic interference aimed at reducing gastric tumor burden. Hence, in accordance with the present invention, IL-11 and IL-11R antagonists are proposed to be useful in the treatment of gastrointestinal-type cancers such as GC or colorectal cancer.

Accordingly, the present invention provides a method for the treatment of a gastrointestinal-type cancer in a subject, the method comprising administering to the subject an antagonist of IL-11 or IL-11R.

In another aspect, the present invention is directed to a method for the treatment of GC in a subject, the method comprising administering to the subject an antagonist of IL-11 or IL-11R.

The present invention is further directed to a method for the treatment of colorectal cancer in a subject, the method comprising administering to the subject an antagonist of IL-11 or IL-11R.

The antagonists are provided in an effective amount. Accordingly, the present invention provides a method for the treatment of a gastrointestinal-type cancer in a subject, method comprising administering to the subject an effective amount of an antagonist of IL-11 or IL-11R.

In another aspect, the present invention is directed to a method for the treatment of GC in a subject, the method comprising administering to the subject an effective amount of an antagonist of IL-11 or IL-11R.

In still yet another aspect, the present invention is directed to a method for the treatment of colorectal cancer in a subject, the method comprising administering to the subject an effective amount of an antagonist of IL-11 or IL-11R.

Reference to "IL-11 or IL-11R" includes "IL-11 and/or IL-11R"

Reference to "effective amount" includes an effective amount or an amount sufficient to ameliorate symptoms of the gastrointestinal-type cancer, and in particular GC or colorectal cancer. Alternatively, the effective amount is the amount required to down-regulate activation of STAT3.

As indicated above, the terms "effective amount" and "therapeutically effective amount" mean a sufficient amount of an agent which provides the desired therapeutic or physiological effect or outcome including inhibiting the activity of IL-11 or of IL-11/IL-11R signaling. The inhibitory effect includes inhibiting or reducing STAT3 and/or STAT1 activation. In addition, the effect may be an amelioration of the symptoms of a gastrointestinal-type cancer such as GC or colorectal cancer. Undesirable side effects may sometimes manifest along with the desired therapeutic effect; hence, a practitioner balances the potential benefits against the potential risks in determining what is an appropriate "effective amount". The exact amount of agent required may vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. For example, the ability of an IL-11 mutein, an anti-IL-11 antibody or an anti-IL-11R antibody or another agent acting as an IL-11/IL-11R antagonist to ameliorate the effects of cancer can be evaluated in an animal model system such as the gp130$^{Y757F/Y757F}$ mouse. One of ordinary skill in the art would be able to determine the required amounts based on such factors as the subject's size, the severity of the subject's symptoms, and the particular composition or route of administration selected.

Insofar as one embodiment of the present invention relates to the use of an IL-11 mutein, an anti-IL-11 antibody or an anti-IL-11R antibody or other IL-11 or IL-11R antagonist, the effective amount includes from about 10 µg/kg body weight to 20 mg/kg body weight of antibody such as 10, 20, 30, 40, 50, 60, 70, 80, 90, 100 µg/kg body weight, 100, 200, 300, 400, 500, 600, 700, 800, 900, 1000 µg/kg body weight or 2, 3, 4, 5, 6, 7, 8, 9, 10, 11, 12, 13, 14, 15, 16, 17, 18, 19 or 20 mg/kg body weight. Similar amounts are provided for single or combination therapy.

The effective amount may also be described in terms of functional effects. Hence, the amount of IL-11 or IL-11R antagonist can be defined in terms of an amount sufficient to inhibit or reduce STAT3 activation. Alternatively, the amount is sufficient to inhibit gastric tumorigenesis and/or inflammatory aspects of gastric tumorigenesis. Still in another embodiment, the amount is sufficient to ameliorate the symptoms of GC. This may be manifested as a reduction in gastric tumor burden. Yet still in another embodiment, the amount is sufficient to ameliorate the symptoms of colorectal cancer.

The effective amount is conveniently described in terms of "for a time and under conditions sufficient to have the effect". This encompasses multiple doses over time and using particular types of formulations.

The term "an antagonist of IL-11 or IL-11R" as used herein means an agent that binds or associates to IL-11 or IL-11R and directly inhibits the formation on cells of a multimeric receptor complex that incorporates IL-11, IL-11R and gp130, thus inhibiting IL-11 signaling through the IL-11 receptor complex. Examples of such antagonists of IL-11 or IL-11R are an IL-11 mutein, an antibody specific for IL-11, an antibody specific for IL-11R and a soluble IL-11R The term also includes agents that specifically inhibit expression of IL-11 or IL-11R, for example antisense polynucleotides that specifically recognise a polynucleotide encoding IL-11 or the IL-11 receptor, interfering RNA that disrupt expression of IL-11 or the IL-11 receptor or ribozymes that specifically recognise a polynucleotide encoding IL-11 or the IL-11 receptor.

Antagonists of IL-11 or IL-11R are known in the art, for example U.S. Pat. No. 6,998,123 describes a soluble IL-11R, IL-11-binding portions thereof, and commercially available antibodies to IL-11 and demonstrates their antagonist activity. Soluble forms of IL-11R are also described in U.S. Pat. No. 6,528,281. International Patent Publication No. WO 03/099322 describes certain IL-11 muteins and demonstrates their antagonist activity.

The term "IL-11" or its full name "interleukin-11" as used herein includes all mature forms of wild type mammalian IL-11, including human, murine and macaque, and all truncated forms of IL-11 molecules which retain IL-11 activity, i.e. the ability to bind or associate with IL-11R and form a functional receptor complex with gp130. Mature human IL-11 is a 178 amino acid protein (i.e. lacking the 21 amino acid leader sequence of NP_000632, NCBI protein database Accession Number), and mature murine IL-11 is a 178 amino acid protein (i.e. lacking the 21 amino acid leader sequence of NP_032376, NCBI protein database Accession Number).

The term "IL-11R" or its full name "interleukin-11 receptor" as used herein includes, but is not limited to, human IL-11R having the nucleotide and amino acid sequences disclosed in SEQ ID NOs:1 and 2 of International Patent Publication No. WO 96/19574 and murine IL-11R having the nucleotide and amino acid sequences disclosed in SEQ ID NOs:2 and 3 of International Patent Publication No. WO 96/07737. IL-11R is also known as IL-11Rα1 and IL-11Rα and the terms may be used interchangeably.

The term "IL-11 mutein" as used herein refers to modified forms of mature IL-11 in which the amino acid sequence has been altered to retain effective binding to IL-11R but inhibit the formation of an IL-11 receptor complex with gp130. Such muteins compete with IL-11 for IL-11R binding and antagonize IL-11 signaling thereby inhibiting IL-11 action. Alterations to the sequence to form a mutein include amino acid substitutions of important residues for receptor binding. Conveniently, the mutein is based on human or murine IL-11, and more particularly human IL-11. WO 03/099322 describes certain IL-11 muteins and demonstrates their antagonist activity. Muteins may be expressed in suitable host cells and purified using standard techniques. IL-11 muteins may be further modified, for example, to increase their in vivo half life, including for, example, by the attachment of other elements such as a Polyethyleneglycol (PEG) groups. Methods for the PEGylation of peptides are well known in the art.

The terms "antagonist", "agent", "medicament" and "active" may be used interchangeably herein to refer to a substance that induces a desired pharmacological and/or physiological effect, and may include the IL-11 and IL-11R antagonists described herein. The pharmacological and/or physiological effect includes inhibiting GC and/or IL-11-dependent activation of STAT3 and/or inhibiting the IL-11-dependent promotion of inflammation-associated gastric tumorigenesis and/or colorectal cancer. The terms also encompass pharmaceutically acceptable and pharmacologically active forms thereof, including salts. The desired effect is the inhibition of IL-11 activity or IL-11 receptor complex signaling.

The terms "cancer" and "tumor" may be used interchangeably herein.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')$_2$ fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies, humanized antibodies or primatized antibodies. It also includes other forms of antibodies that may be therapeutically acceptable and antigen-binding fragments thereof, for example single domain antibodies derived from cartilage marine animals or Camelidae, or from libraries based on such antibodies.

The term "monoclonal antibody" is used herein to refer to an antibody obtained from a population of substantially homogeneous antibodies. That is, the individual antibodies comprising the population are identical except for naturally occurring mutations that may be present in minor amounts. The modifier "monoclonal" as used herein therefore indicates the character of the antibody as being obtained from a substantially homogeneous population of antibodies, and is not used to indicate that the antibody was produced by a particular method. For example, monoclonal antibodies in accordance with the present invention may be made by the hybridoma method described by Kohler and Milstein, *Nature* 256: 495-499, 1975, or may be made by recombinant DNA methods (such as described in U.S. Pat. No. 4,816,567). Monoclonal antibodies may also be isolated from phage antibody libraries using the techniques described in Clackson et al, *Nature* 352:624-628, 1991 or Marks et al, *J. Mol. Biol.* 222:581-597, 1991.

Chimeric antibodies may include antibodies to IL-11 or IL-11R comprising the heavy and light chain variable regions of mouse, rat or rabbit antibodies to IL-11 or IL-11R and human heavy and light chain constant domains.

Reference to a "gastrointestinal-type cancer" includes "gastrointestinal cancer" and, as indicated above encompasses cancer of the oesophagus, liver, biliary system, pancreas, bowels and anus. In a particular embodiment, the gastrointestinal-type cancer is GC. In another embodiment, the gastrointestinal-type cancer is colorectal cancer.

The IL-11 and IL-11R antagonists used in accordance with the present invention may be administered as part of a pharmaceutical composition.

In one embodiment, a method of treating a gastrointestinal-type cancer in a subject is provided, the method comprising administering to the subject an effective amount of a pharmaceutical composition comprising an IL-11 or IL-11R antagonist formulated with a pharmaceutically acceptable carrier and/or diluent.

In another embodiment, the present invention contemplates a method for treating GC in a subject, the method comprising administering to the subject an effective amount of a pharmaceutical composition comprising an IL-11 or IL-11R antagonist formulated with a pharmaceutically acceptable carrier and/or diluent.

In still another embodiment, the present invention provides a method for treating colorectal cancer in a subject, the method comprising administering to the subject an effective amount of a pharmaceutical composition comprising an IL-11 or IL-11R antagonist formulated with a pharmaceutically acceptable carrier and/or diluent.

A "pharmaceutically acceptable" carrier and/or diluent is a pharmaceutical vehicle comprised of a material that is not biologically or otherwise undesirable, i.e. the material may be administered to a subject along with the selected active agent without causing any or a substantial adverse reaction. Carriers may include any and all solvents, dispersion media, coatings, antibacterial and antifungal agents, agents used for adjusting tonicity, buffers, chelating agents, and absorption delaying agents and the like.

Similarly, a "pharmacologically acceptable" salt of a compound as provided herein is a salt that is not biologically or otherwise undesirable.

The terms "treating" and "treatment" as used herein refer to therapeutic treatment. For example, treatment may result in a reduction in severity and/or the frequency of symptoms of the gastrointestinal-type cancer such as GC or colorectal cancer, the elimination of symptoms and/or underlying cause of the tumorigenesis, the prevention of the occurrence of symptoms of inflammation and/or their underlying cause and improvement or remediation or amelioration of damage following inflammation. Hence, the treatment may not result in a "cure" but rather an amelioration of symptoms including a reduction in the gastric tumor burden in a subject. In addition, treatment may not commence until an exacerbated event occurs. In this context, the term "prophylaxis" also applies to the prevention or treatment of a likelihood of an exacerbated event occurring.

The terms "treating" and "treatment" as used herein also refer to the reduction of one or more symptoms or characteristics associated with gastrointestinal-type cancers such as GC or colorectal cancer.

The terms "condition" and "disease" are used interchangeably throughout the subject specification.

A "subject" as used herein refers particularly to a human but also extends to any animal, including a mammal who can benefit from the pharmaceutical compositions and methods of the present invention. Other useful mammals contemplated herein are laboratory test animals, examples of which include mice, rats, rabbits, guinea pigs, hamsters, cats and dogs. There is no limitation on the type of animal that could benefit from the presently described pharmaceutical compositions and methods. A subject regardless of whether a human or non-human animal may be referred to as an individual, patient, animal or recipient as well as subject. The methods of the present invention have applications in human medicine and veterinary medicine.

As indicated above, one useful antagonist for use in the present invention is an IL-11 mutein. International Patent Publication No. WO 03/099322 describes certain IL-11 muteins and demonstrates their antagonist activity.

In one aspect, the present invention contemplates a method for the treatment of a gastrointestinal-type cancer in a subject, the method comprising administering to the subject an amount of an IL-11 mutein effective to inhibit the activity of IL-11.

In another aspect, the present invention provides a method for the treatment of GC in a subject, the method comprising administering to the subject an amount of an IL-11 mutein effective to inhibit the activity of IL-11.

In yet another aspect of the present invention is directed to a method for the treatment of colorectal cancer in a subject, the method comprising administering to the subject an amount of an IL-11 mutein effective to inhibit the activity of IL-11.

In these aspects, the IL-11 mutein is administered for a time and under conditions sufficient to reduce IL-11-mediated signaling such as to reduce STAT3 and/or STAT1 activation.

In one aspect, the IL-11 mutein comprises the amino acid sequence set forth in SEQ ID NO:1, SEQ ID NO:2, SEQ ID NO:3 or SEQ ID NO:4.

Another useful agent is a soluble IL-11R which competes with the naturally occurring membrane-associated IL-11R for IL-11 interaction. Those skilled in the art can readily prepare soluble forms of the receptor, see, for example, U.S. Pat. Nos. 6,528,281 and 6,998,123. Soluble IL-11R comprises the portion of the extracellular region of IL-11R that is required to bind IL-11, and include sequences derived from that sequence that have 95% or greater identity to that sequence when aligned, and allowing for any gaps to maximise alignment. In a particular embodiment, soluble forms of IL-11R comprise the two fibronectin domains of the extracellular region of the human IL-11 receptor, also known as domains 2 and 3. Conveniently, the soluble receptor is modified to improve the affinity for IL-11 over and above the affinity of naturally occurring IL-11R, either by addition, deletion or substitution of from 1 to 10 amino acids, or by fusion to other peptide fragments, for example Fc fragments derived from human immunoglobulins, including modified forms of such fragments known to those skilled in the art, or domains 1-3 of the extracellular region of human gp130 with a linker between the peptides to allow for appropriate folding. The latter approach provides a high affinity soluble IL-11R; similar to the soluble receptors for IL-6 reported by Ancey et al., J Biol Chem 278(19):16968-16972, 2003. In addition, IL-11 cytokine traps are included in the term soluble IL-11R. Such IL-11 cytokine traps comprise a fusion peptide comprising the extracellular region of IL-11R that is required to bind IL-11, an Fc fragment, domains 1-3 of the extracellular region of human gp130, with appropriate linker sequences between the various components, and each of the components (i.e. segment of IL-11R, Fc and gp130) may contain from 1 to 10 amino acid additions, deletions or substitutions; examples of cytokine traps are found in International Patent Publication Nos. WO 95/11303, WO 99/61630 and WO 00/18932. Soluble forms of IL-11R may be expressed in suitable host cells and purified using standard techniques.

In one aspect, the present invention contemplates a method for the treatment of a gastrointestinal-type cancer in a subject, the method comprising administering to the subject an amount of a soluble IL-11R effective to inhibit the activity of IL-11.

In another aspect, the present invention contemplates a method for the treatment of GC in a subject, the method comprising administering to the subject an amount of a soluble IL-11R effective to inhibit the activity of IL-11.

Still a further aspect of the present invention is directed to a method for the treatment of colorectal cancer in a subject, the method comprising administering to the subject an amount of a soluble IL-11R effective to inhibit the activity of IL-11.

In an embodiment the soluble IL-11R is derived from human IL-11R.

Another useful antagonist for use in the present invention is an antibody specific for either IL-11 or IL-11R which inhibits IL-11 action; i.e. inhibits IL-11 signaling through the IL-11 receptor complex by inhibiting the formation of a multimeric receptor complex that incorporates IL-11, IL-11R and gp130. Such antibodies to IL-11 may be referred to as anti-IL-11 antibodies, and antibodies to IL-11R may be referred to as anti-IL-11R antibodies.

The antibodies may be polyclonal or monoclonal antibodies and methods for their isolation production and administration would be known to the skilled artisan. Monoclonal antibodies are particularly useful.

The anti-IL-11 or anti-IL-11R antibodies, for example, may also be produced using recombinant methods (for example, in an *E. coli* expression system or other suitable host cell) well known in the art such as described in U.S. Pat. Nos. 4,399,216; 4,912,040; 4,740,461 and 4,959,455.

Chimeric forms of murine anti-IL-11 or anti-IL-11R monoclonal antibodies may also be produced by replacing the nucleotides encoding selected murine heavy and light chain constant domains with nucleotides encoding human heavy and light chain constant domains, such as is described in U.S. Pat. No. 4,816,567 and by Morrison et al, *Proc. Nat. Acad. Sci.* 81:6851, 1984. The chimeric antibodies may then be produced in an appropriate cell line, such as a murine myeloma or CHO cell line, that has been transfected with modified DNA.

Thus, among the antibodies contemplated for use in the present invention are chimeric anti-IL-11 or anti-IL-11R antibodies that comprise the heavy and light chain variable regions of murine anti-IL-11 or anti-IL-11R monoclonal antibody fused to human heavy and light chain antibody constant domains. Similarly, chimeric antibodies may include antibodies to IL-11 or IL-11R comprising the heavy and light chain variable regions of other non-human animal (for example rat or rabbit) antibodies to IL-11 or IL-11R and human heavy and light chain constant domains.

The anti-IL-11 or anti-IL-11R antibodies for use in the present invention also include humanized antibodies. In general, humanized antibodies are human antibodies (the recipient antibody) in which the complementarity determining (CDR) region residues have been replaced by CDR region residues from a non-human species (the donor antibody), such as from a mouse, rat, rabbit or non-human primate. In some cases, certain framework region (FR) residues of the human antibody may also be replaced by corresponding non-human residues, or the humanized antibodies may comprise residues which are not found in the recipient antibody or in the donor antibody. These modifications are made to enhance antibody performance and affinity. In general, the humanized antibody will comprise substantially all of at least one, and typically two, variable regions, in which all or substantially all of the CDR regions correspond to those of a non-human antibody, and all or substantially all of the FRs are those of a human antibody sequence. The humanized antibody may also optionally comprise at least a portion of an antibody constant region (Fc), typically that of a human antibody. Similarly, to create a primatized antibody the murine CDR regions can be inserted into a primate framework using methods known in the art (see e.g. WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al, *Mol. Immunol.* 28:489-498, 1991 and Pedersen et al, *J. Mol. Biol.* 235:959-973, 1994).

Further, International Patent Publication No. WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments.

Other approaches to producing humanized antibodies are known to those in the art that may use frameworks that are substantially human, or composites of human frameworks.

The CDRs of a given antibody may be readily identified, for example using the system described by Kabat et al in *Sequences of Proteins of Immunological Interest*, 5th Ed., US Department of Health and Human Services, PHS, NIH, NIH Publication No. 91-3242, 1991).

In one embodiment, the antibodies for use in the present invention are human monoclonal antibodies. Such human monoclonal antibodies directed against IL-11 or its receptor can be generated using transgenic or transchromosomic mice carrying parts of the human immune system rather than the mouse system. These transgenic and transchromosomic mice include mice referred to herein as HuMAb mice and KM mice.

Still further, alternative transgenic animal systems expressing human immunoglobulin genes are available in the art and can be used to raise antibodies. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963.

Human monoclonal antibodies can also be prepared using phage display or other display methods for screening libraries of human immunoglobulin genes. Such display methods for isolating human antibodies are established in the art. See for example: U.S. Pat. Nos. 5,223,409; 5,403,484; and 5,571,698; 5,427,908 and 5,580,717; 5,969,108 and 6,172,197 and 5,885,793; 6,521,404; 6,544,731; 6,555,313; 6,582,915 and 6,593,081.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

The anti-IL-11 or anti-IL-11R antibodies of the present invention also include antigen-binding fragments such as Fv, Fab, Fab' and F(ab')$_2$ fragments. A number of methods have now been developed for producing antigen-binding fragments of antibodies.

For example, Fab'-SH fragments can be directly recovered from *E. coli* and chemically coupled to form F(ab')$_2$ fragments (Carter et al, *Bio/Technology* 10:163-167, 1992). F(ab')$_2$ fragments can also be formed using the leucine zipper GCN4 to promote assembly of the F(ab')$_2$ molecule. Fv, Fab or F(ab')$_2$ fragments can also be isolated directly from recombinant host cell cultures. A number of recombinant methods have been developed for the production of single chain antibodies including those described in U.S. Pat. No. 4,946,778; Bird, *Science* 242:423, 1988; Huston et al, *Proc. Natl. Acad. Sci. USA* 85:5879, 1988 and Ward et al, *Nature* 334:544, 1989. Single chain antibodies may be formed by linking heavy ($V_H$) and light ($V_L$) chain variable region (Fv region) fragments via an short peptide linker to provide a single polypeptide chain (scFvs). The scFvs may also form dimers or trimers, depending on the length of a peptide linker between the two variable regions (Kortt et al, *Protein Engineering* 10:423, 1997). Phage display is another well known recombinant method for producing the antigen-binding fragments of the present invention.

Antigen-binding fragments for use in the present invention may be screened for desired properties and assays to identify antigen-binding fragments that bind to IL-11 or IL-11R and which antagonize IL-11 signaling through the IL-11R complex are known in the art.

Mammalian cell lines available as host cells for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used as host cells are insect cell lines, such as Sf9 cells, amphibian cells, bacterial cells, plant cells and fungal cells. Standard techniques are used for the culture of the host cells and expression of the desired peptide. For example, when recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies or other peptides can be recovered from the culture medium using standard protein purification methods. Further, expression from host cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846; 0 256 055 and 0 323 997 and European Patent Application No. 89303964.4.

In one aspect, the present invention relates to a method for the treatment of a gastrointestinal-type cancer in a subject, the method comprising administering to the subject an amount of an anti-IL-11 antibody or anti-IL-11R antibody effective to inhibit IL-11 signaling.

In another aspect, the present invention contemplates a method for the treatment of GC in a subject, the method comprising administering to the subject an amount of an anti-IL-11 antibody or anti-IL-11R antibody effective to inhibit IL-11 signaling.

Yet another aspect of the present invention provides a method for the treatment of colorectal cancer in a subject, the method comprising administering to the subject an amount of an anti-IL-11 antibody or anti-IL-11R antibody effective to inhibit IL-11 signaling.

As indicated above, the antibodies for use in the method of the present invention include human or humanized anti-IL-11 or anti-IL-11R antibodies.

The present invention contemplates combination therapy such as using an IL-11 or IL-11R antagonist in combination with one or more other anti-cancer agents or anti-cancer protocols such as chemotherapy, radiation therapy or surgical ablation of cancer tissue.

Accordingly, another aspect of the present invention contemplates a method for the treatment of a gastrointestinal-type cancer in a subject, the method comprising administering an antagonist of IL-11 or IL-11R together with at least one other therapeutic agent and/or in combination with chemotherapy, radiation therapy and/or surgical ablation of cancer tissue.

In another aspect, the present invention provides a method for the treatment of GC in a subject, the method comprising administering an antagonist of IL-11 or IL-11R together with at least one other therapeutic agent and/or in combination with chemotherapy, radiation therapy or surgical ablation of cancer tissue.

The present invention further provides a method for the treatment of colorectal cancer in a subject, the method comprising administering an antagonist of IL-11 or IL-11R together with at least one other therapeutic agent and/or in combination with chemotherapy, radiation therapy or surgical ablation of cancer tissue.

As indicated above, useful antagonists include an IL-11 mutein, an anti-IL-11 or anti-IL-11R antibody, and a soluble IL-11R. Reference to "together with" includes simultaneous or sequential treatments.

Antagonists of IL-11 or IL-11R (e.g. antibodies, proteins such as non-signaling mutant forms of IL-11 (IL-11 muteins), soluble IL-11 receptors, etc) for use in the present invention are conveniently supplied in pharmaceutical compositions.

Administration may be systemic or local. Systemic administration is particularly useful. Reference to "systemic administration" includes intra-arterial, intravenous, intraperitoneal, and subcutaneous injection or infusion, as well as administration via oral, rectal and nasal routes, or via inhalation.

Compositions suitable for systemic use include sterile aqueous solutions (where water soluble), sterile powders for the extemporaneous preparation of sterile injectable solutions, and sterile powders for inhalation. It must be stable under the conditions of manufacture and storage and must be preserved against the contaminating action of microorganisms such as bacteria and fungi. The carrier can be any pharmaceutically acceptable carriers and/or diluent, for example, water, ethanol, polyol (for example, glycerol, propylene glycol and liquid polyethylene glycol, and the like), suitable mixtures thereof and vegetable oils. The proper fluidity can be maintained, for example, by the use of superfactants. Various anti-bacterial and anti-fungal agents, for example, parabens, chlorobutanol, phenol, sorbic acid, thirmerosal and the like may be included. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin.

Sterile solutions are prepared by incorporating the active in the required amount in the appropriate solvent and optionally with other active ingredients and excipients as required, followed by filtered sterilization or other appropriate means of sterilization. In the case of sterile powders, suitable methods of preparation include vacuum drying and the freeze-drying technique which yield a powder of active ingredient plus any additionally desired ingredient which can be made at an appropriate particle size.

When the active is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like.

Dosage regimens may be adjusted to provide the optimum desired response (e.g. a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the antagonist, employed in the pharmaceutical composition, at levels lower than that required in order to achieve the desired therapeutic effect and gradually increase the dosage until the desired effect is achieved. In general, a suitable dose of a composition of the invention may be that amount of the compound which is the lowest dose effective to produce a therapeutic effect.

The present invention further contemplates the use of an antagonist of IL-11 or IL-11R in the manufacture of a medicament for the treatment of a gastrointestinal-type cancer.

In another aspect, the present invention provides for the use of an antagonist of IL-11 or IL-11R in the manufacture of a medicament for the treatment of GC in a subject.

The present invention also provides for the use of an antagonist of IL-11 or IL-11R in the manufacture of a medicament for the treatment of colorectal cancer in a subject.

Useful antagonists include an IL-11 mutein, an anti-IL-11 or anti-IL-11R antibody, and a soluble IL-11R.

In another aspect, the present invention is directed to the use of an IL-11 mutein, an antibody specific for IL-11 or specific for IL-11R, or a soluble IL-11R in the manufacture of a medicament for the treatment of a gastrointestinal-type cancer such as GC in a subject.

In yet another aspect, the present invention contemplates the use of an IL-11 mutein, an antibody specific for IL-11 or specific for IL-11R, or a soluble IL-11R in the manufacture of a medicament for the treatment of a gastrointestinal-type cancer such as colorectal cancer in a subject.

The methods of the present invention may optionally include a step of selecting subjects with an indicator of a gastrointestinal-type cancer, for example GC, prior to treatment with an antagonist of IL-11 or IL-11R.

Animal models useful for testing of antagonists of IL-11 or IL-11 receptor include the gp130$^{Y757F/Y757F}$ mouse.

A medical kit is also provided comprising an antagonist of IL-11 or IL-11R together with instructions to use the antagonists in the treatment of a gastrointestinal cancer such as GC or colorectal cancer.

Another aspect of the present invention is directed to a therapeutic protocol for treating GC in a subject, the protocol comprising screening a biopsy of gastric tissue for expression levels of IL-11 and in subjects having tissue with high IL-11 expression, providing an IL-11 or IL-11R antagonist for a time and under conditions to reduce potential tumorigenesis and/or to ameliorate gastric tumor burden.

The present invention also provides a therapeutic protocol for treating colorectal cancer in a subject, the protocol comprising screening a biopsy of colorectal tissue for expression levels of IL-11 and in subjects having tissue with high IL-11 expression, providing an IL-11 or IL-11R antagonist for a time and under conditions to reduce potential tumorigenesis and/or to ameliorate colorectal tumor burden.

The present invention is further described by the following non-limiting Examples. In the Examples the following methods are employed.

Mice and treatments. Mice homozygous for the gp130 ($Y_{757}F$) knock-in mutation (gp130$^{Y757F/Y757F}$), as well as their corresponding compound mutant derivatives lacking either the IL-6 (gp130$^{Y757F/Y757F}$:IL-6$^{-/-}$) or IL-11Rα1 (gp130$^{Y757F/Y757F}$:IL-11Rα1$^{-/-}$) genes were generated as previously described (Jenkins et al, 2007 supra; Howlett et al, 2005 supra). All animals were housed under specific pathogen-free conditions and included wild-type (gp130$^{+/+}$) littermate controls that were genetically matched.

Antibodies. Commercially available antibodies against IL-11, gp130, Erk1/2, STAT1, STAT3 were purchased from Santa Cruz Biotechnology (Santa Cruz, Calif.), while phospho(Tyr701)STAT1 and phospho(Tyr705)STAT3 antibodies were from Santa Cruz Biotechnology (Santa Cruz, Calif.) and Cell Signaling Technologies (Beverly, Mass.). Anti-CD45 was from BD Pharmingen (San Jose, Calif.).

Histological and immunohistochemical analyses. Following dissection, stomach specimens were fixed in 10% v/v neutral-buffered formalin (pH 7.4) solution and embedded in paraffin. For general histology, sections were stained with hematoxylin and eosin (H and E) Immunohistochemical stainings were performed with antibodies against CD45, pY-STAT3 and the proliferating cell nuclear antigen (PCNA; DakoCytomation, Carpinteria, Calif.) on sections of untreated mice. Cellular proliferation was also assessed by staining with an anti-BrdU antibody (BD Pharmingen, San Jose, Calif.) of tissues collected 4 h after injection of 50 µg/kg bromodeoxyuridine (BrdU; Amersham). In each case immunoperoxidase staining was detected with the Liquid Diaminobenzidine (DAB) Substrate Chromogen System (DakoCytomation, Carpinteria, Calif.), and sections were counterstained with hematoxylin.

Gastric polyps (tumors) were classified and enumerated according to their size and carefully excised to determine their wet-weight, and either snap frozen for RNA/protein analysis or formalin-fixed for histological and immunohistochemical analysis.

At post-mortem, the entire colon was excised and measured from the cecum to the anus, and colon length was recorded as a marker of inflammation. The colon was then opened longitudinally, and individual macroscopic colon polyps (tumors) were classified and enumerated according to their size. In a subset of samples a portion of the distal colon was dissected in half (longitudinally) and snap frozen for RNA and protein analysis. The remaining colon of each sample was rolled ("swiss roll") and formalin-fixed, as for stomach specimens, for histological and immunohistochemical analysis of the entire colon. The polyp burden was further enumerated from serial sections of H and E stained slides to encorporate microscopic tumour burden.

Molecular analysis. Quantitative RT-PCR (Q-PCR) gene expression analyses were performed on triplicate samples with SYBR Green (Invitrogen) using the 7900HT Fast RT- PCR System (Applied Biosystems, Foster City, Calif.) over 40 cycles (95° C./15 sec, 60° C./1 min), following an initial denaturation step at 95° C./10 min. Primers to specifically amplify 18S were used to normalize cDNA concentrations of target genes. Data acquisition and analyses were performed with the Sequence Detection System Version 2.3 software (Applied Biosystems).

Statistical analyses. Comparisons between mean values were performed using Anova and Student's t-tests as appropriate. A P value of less than 0.05 was considered statistically significant.

Production of IL-11 mutein. An IL-11 mutein of SEQ ID NO: 1 (in which the amino acid sequence AMSAG at positions 58-62 of mature murine IL-11 has been replaced with the amino acid sequence PAIDY and the tryptophan at position 147 of mature murine IL-11 has been replaced with alanine) was expressed in E. coli as an N-terminal His-tagged protein.

Briefly, cDNA encoding the mutein was PCR amplified and sub-cloned into a modified version of the pET15b vector (Novagen Cat # 69661-3). The pET15b vector was modified by replacing the thrombin cleavage site and the multiple cloning site with AscI and EcoRI restriction sites, and to include an M13 origin of replication (enabling the vector to be used as a phagemid). The E. coli strain BL21-CodonPlus [Registered trade mark](DE3)-RIL E. coli (Strategene cat #230245) was transformed with the pET15b—mutein construct and grown in a 400 mL shake-flask culture in superbroth containing 2% v/v glucose and 100 µg/mL ampicillin was grown to an optical density (600 nm) of 0.5. Protein expression was induced by the addition of isopropyl-β-D-thiogalactopyranoside to a final concentration of 200 uM and the culture was incubated with shaking at 37° C. for a further 4 hours. The expressed N-terminal hexahistidine-tagged mutein was purified from the E. coli cells (lysed in 7 M guanidinium hydrochloride) using immobilized nickel ion affinity chromatography and refolded by dialysis into PBS. Refolded samples of tagged mutein were further dialysed against 0.15% v/v aqueous trifluoroacetic acid, and purified by reverse phase HPLC using acetonitrile gradients in 0.15% v/v trifluoroacetic acid. Samples were then lyophilized and reconstituted in a small volume of water prior to dilution with buffer.

A competition ELISA demonstrated that the binding affinity of mutein for IL-11R-Fc was approximately 20-fold higher than the binding affinity of murine W147A IL-11 for IL-11R-Fc. MurineW147A IL-11 (i.e. IL-11 in which the tryptophan at position 147 has been replaced with alanine) has been previously characterized as an antagonist of IL-11 bioactivity (Underhill-Day et al, Endocrinology 144; 3406-3414, 2003).

In vitro activity of mutein. An IL-11 responsive cell line, Ba/F3 cells stably transfected with murine IL-11R/gp130, was seeded at $3\times10^4$ cells/well in 50 uL of Dulbecco's modified Eagle's medium containing 10% v/v fetal calf serum and increasing concentrations of mutein or W147A IL-11 were added in the presence of a fixed, submaximal concentration of murine IL-11 (50 µM) in a total volume of 100 uL/well. After incubation for 48 hours, proliferation was measured colorimetrically at 570 nm using 3-(4,5-dimethylthiazol-2-yl)-2,5-diphenyl tetrazolium bromide (MTT; Sigma-Aldrich). All assays were performed in duplicate and the mean values for each assay point were plotted.

Murine W147A IL-11 was able to inhibit murine IL-11 induced cell proliferation of the BaF3 cells in a dose-dependent manner. The mutein of the present example was significantly more potent at blocking murine IL-11 induced cell proliferation of the BaF3 cells, being 20 to 30-fold more potent an antagonist of murine IL-11 than murine W147A IL-11.

PEGylation of mutein. To PEGylate the mutein, a Cys residue was introduced into the sequence at position 147 by site directed mutagenesis to provide a chemically reactive side-chain which can be site-specifically modified with a maleimide-derivatized PEG reagent. Furthermore, the mature murine IL-11 protein sequence has a thrombin cleavage site that results in the removal of the first 9 N-terminal amino acids. The mutein showed identical activity with and without the first 9 N-terminal amino acids so the internal thrombin site was also optimized by site directed mutagenesis by mutating amino acids $^6$Gly and $^7$Ser to $^6$Leu and $^7$Val respectively (SEQ ID NO: 2). For production of PEGylated mutein, the amino-terminal His-tag and the first 9 N-terminal amino acids were removed by thrombin digestion.

Briefly, the mutein comprising SEQ ID NO: 2 was expressed in E. coli and purified and refolded as described above. Lyophilized samples of this mutein were then re-suspended in thrombin cleavage buffer (150 mM NaCl, 2.5 mM $CaCl_2$, 20 mM Tris.HCl pH 8.4) at a concentration of 0.5 mg/mL and treated with 5 units of thrombin/mg protein for 4 hours at room temperature, to produce the mutein of SEQ ID NO: 3, which was then purified by reverse phase HPLC as previously described.

Lyophilized samples were resuspended at a concentration of 5 mg/mL in 1 mM aqueous acetic acid containing 5 mM tris(2-carboxyethyl)phosphine, and mixed with 4 volumes of 12.5 mg/mL mPEG2-maleimide (Nektar Therapeutics cat #2D3YOTO1) in PBS. Reactions were incubated for 16 hours at room temperature and protein-PEG conjugates were separated from unconjugated components by cation exchange chromatography on an SP Sepharose column, using a NaCl gradient in 20 mM sodium acetate, pH 5.5 buffer. Fractions containing the PEGylated products were pooled, dialyzed against 5 mM ammonium acetate buffer, pH 5.5, and then lyophilized.

Analysis of the PEGylated mutein by SDS-PAGE showed a shift in apparent molecular weight consistent with attachment of a single 40 kDa PEG moiety. The IL-11R binding affinity of PEGylated mutein was reduced approximately 5-fold relative to the binding affinity of non-PEGylated mutein, whilst the ability of PEGylated mutein to antagonize IL-11-induced Ba/F3 cell proliferation was reduced approximately 10-fold. The PEGylated mutein was, however, more potent than murine W147A IL-11 in both the IL-11R binding ELISA and the Ba/F3 cell assays.

Part of the data herein was published in Ernst et al, *The J. Clin Invest* 118:1727-1738, 2008, the contents of which are incorporated herein by reference.

EXAMPLE 1

Increased Expression of IL-6 Family Cytokines in Gastric Tumors of $gp130^{Y757F/Y757F}$ Mice IL-11 expression was quantified in tumor-bearing antral tissues from adult $gp130^{Y757F/Y757F}$ mice (aged between 10 and 14 weeks) by quantitative RT-PCR (Q-PCR) and immunoblot analyses. Gastric IL-11 mRNA and protein levels were elevated approximately 30-fold and 15-fold, respectively, in tumors of $gp130^{Y757F/Y757F}$ mice compared to unaffected tissue from $gp130^{+/+}$ wild-type mice. Meanwhile, gene expression for the gp130-acting cytokines IL-6 and LIF was elevated by only 5-fold in these lesions. By contrast, expression of the ligand-specific receptor α-subunits IL-6Rα and IL-11Rα, as well as of the β-subunit gp130 in gastric tissue remained unaffected and was comparable between gp130$^{Y757F/Y757F}$ and gp130$^{+/+}$ mice.

EXAMPLE 2

IL-11 Receptor Signaling is Essential for Gastric Tumorigenesis in gp130$^{Y757F/Y757F}$ Mice Based on the augmented IL-11 expression in gp 130$^{Y757F/Y757F}$ gastric tumors (EXAMPLE 1), a causal link between the gastric phenotype and exaggerated signaling emanating from the IL-11 receptor complex was investigated. IL-11 signaling was inactivated by generating compound mutant gp130$^{Y757F/Y757F}$:IL11Rα1$^{-/-}$ mice which lacked the widely expressed IL-11 specific ligand-binding receptor α-subunit (Jenkins et al, 2007 supra). It was found that the stomachs of these compound mice were tumor-free and indistinguishable in size and cellular morphology from the stomachs of age-matched wild-type mice even when aged beyond 14 weeks. Notably, gastric sections of gp130$^{Y757F/Y757F}$:IL-11Rα1$^{-/-}$ mice were characterized by the absence of chronic inflammatory (lymphoplasmacytoid) cell infiltrates in the submucosa and lamina propria, and did not show any expansion of proliferating (PCNA-positive) gastric cell populations. By contrast, genetic deletion of IL-6 in gp 130$^{Y757F/Y757F}$:IL-6$^{-/-}$ mice failed to suppress tumorigenesis and had no ameliorating effect on the inflammatory cell infiltrates and associated gastric hyperplasia characteristically found in gp 130$^{Y757F/Y757F}$ mice.

EXAMPLE 3

Absence of Gastric Tumors in gp130$^{Y757F/Y757F}$:IL-11Rα1$^{-/-}$ Mice Correlates with Reduced IL-11 Expression and STAT3 Activation The extent of gastric STAT3 activation and the expression level of IL-11 mRNA in gp130$^{Y757F/Y757F}$:IL-11Rα1$^{-/-}$ mice was investigated. Basal STAT3 tyrosine phosphorylation and expression of the bone-fide STAT3 target gene Socs3 (Maritano et al, *Nat. Immunol.* 5:401-409, 2004) were similar between gp130$^{+/+}$ and gp130$^{Y757F/Y757F}$:IL-11Rα1$^{-/-}$ mice, and markedly reduced when compared to tumor-bearing gp130$^{Y757F/Y757F}$:IL-6$^{-/-}$ and gp130$^{Y757F/Y757F}$ mice. Strikingly, the proportion of phosphorylated STAT3 was less pronounced in the forestomach (fundus) than in the antrum, and this was reflected by a modest increase in Socs3 expression observed in the fundus when compared to its antral expression. Gastric expression of IL-11 mRNA was reduced to wild-type levels in tumor-free gp130$^{Y757F/Y757F}$:IL-11Rα1$^{-/-}$ mice, but remained elevated in gp130$^{Y757F/Y757F}$:IL-6$^{-/-}$ mice. These observations indicate that IL-11 was responsible for gastric STAT3 hyperactivation, and that IL-11 may constitute a potential STAT3 target gene whose augmented expression correlates with gastric disease. A tight correlation was observed between the formation of gastric lesions and elevated antral expression of several STAT3 target genes implicated in the pathogenesis of human GC and promoting cellular processes crucial for tumorigenesis, namely cell cycle progression (cyclin D1 and c-myc) survival (Bcl-xL and survivin) [Jenkins et al, 2005 supra; Kanda et al, 2004 supra] and extracellular matrix degradation (Mmp13) [Elnemr et al, *Gastric Cancer* 6:30-38, 2003]. Collectively, the above data show a correlation between the extent of gastric IL-11 expression, STAT3 phosphorylation and the expression level of critical STAT3 target genes implicated in tumorigenesis.

EXAMPLE 4

Effects of IL-11 Mutein in Animal Model

Eight week old gp130$^{Y757F/Y757F}$ mice were treated intraperitoneally with 1 mg of the PEGylated IL-11 mutein described in the methods section, mutein control (PEG only) or PBS only control three times a week (Monday, Wednesday, Friday schedule) for four weeks. At 28 days after first dose, mice were sacrificed and stomachs removed for gross examination of polyp number and weights. The results showing representative data from one of two independent experiments are provided in Table 3.

TABLE 3

Average gastric polyp weight at day 28

| Treatment group | Average Total Polyp weight/animal (grams) ± stdev |
|---|---|
| PBS (n = 4) | 0.23 g ± 0.05§ |
| IL-11 mutein (n = 8) | 0.06 g ± 0.05†§ |
| Control (n = 4) | 0.28 g ± 0.09† |

§p = 0.0004
†p = 0.0001

Interestingly, a group of animals that were treated with IL-11 mutein for four weeks as noted above, followed by a further 4 weeks without further treatment with IL-11 mutein exhibited an increase in average total polyp weight compared to treated animals. Suggesting that withdrawal of the IL-11 mutein allowed further tumor growth.

EXAMPLE 5

Absence of Colon Tumors in gp130$^{Y757F/Y757F}$:IL-11Rα1$^{-/-}$ Mice

The effects of IL-6 and IL-11 on the development of colorectal cancer were explored in a colitis associated cancer (CAC) model where mice are administered azoxymethane (AOM) followed by dextran sodium sulfate (DSS) (Greten et al, 2004).

The CAC model was performed essentially as described before (Greten et al, 2004) using gp130$^{Y757F/Y757F}$ mice, gp130$^{Y757F/Y757F}$:IL-6$^{-/-}$ mice, gp130$^{Y757F/Y757F}$:IL11Rα1$^{-/-}$ mice and wild type mice, in each case using 10 mg/kg AOM (Sigma-Aldrich) and 2.5% DSS (MP Biomedicals).

The colons of the IL11Rα1$^{-/-}$ mice had fewer tumors than those of the gp130$^{Y757F/Y757F}$ mice, gp130$^{Y757F/Y757F}$:IL-6$^{-/-}$ mice, and wild type mice.

The results show that by six weeks, gp130$^{Y757F/Y757F}$ mice develop gastric tumors. Using genetic knock-out studies, the gp130 signaling cytokine required for the initiation of these tumors was identified as IL-11. An antagonist of IL-11 or IL-11R inhibited and/or reversed established tumors. Surprisingly, inhibiting IL-11 not only prevented new tumor formation, it also regressed pre-formed gastric tumors. Studies in an animal model of colorectal cancer also support the importance of IL-11 in colorectal cancer development. Hence, antagonizing IL-11-mediated signaling is proposed to be useful in the treatment of colorectal cancer. This identifies a potent therapy for the treatment of GC and colorectal cancer.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

Ancey et al., *J Biol Chem* 278(19):16968-16972, 2003
Becker et al, *Cell Cycle* 4:217-220, 2005
Bird, *Science* 242:423, 1988
Boivin et al, *Lab Invest.* 74:513-518, 1996
Carter et al, *Bio/Technology* 10:163-167, 1992
Clackson et al, *Nature* 352:624-628, 1991
Elnemr et al, *Gastric Cancer* 6:30-38, 2003
Ernst et al, *The J. Clin Invest* 118:1727-1738, 2008
Gerhartz et al, *J. Biol Chem.* 271:12991-12998, 1996
Gong et al, *Clin Cancer Res.* 11:1386-1393, 2005
Greten et al, *Cell,* 118: 285-296, 2004
Guilford et al, *Nat Med* 392:402-405, 1998
Heinrich et al, *Biochem J* 334(Pt 2):297-314, 1998
Heinrich et al, *Biochem J* 374:1-20, 2003
Hertzog et al, *Clin Immunol Immunopathol* 58:18-32, 1991
Howlett et al, *Gastroenterology* 129:1005-1018, 2005
Huston et al, *Proc. Natl. Acad. Sci. USA* 85:5879, 1988
Jenkins et al, *Nat Med* 11:845-852, 2005
Jenkins et al, *Blood* 109:2380-2388, 2007
Kabat et al in *Sequences of Proteins of Immunological Interest,* 5th Ed., US Department of Health and Human Services, PHS, NIH, NIH Publication No. 91-3242, 1991
Kanda et al, *Oncogene* 23:4921-4929, 2004
Kanai et al, *Oncogene* 22:548-554, 2003
Kohler and Milstein, *Nature* 256:495-499, 1975
Kishimoto et al, *Blood* 86:1243-1254, 1995
Kortt et al, *Protein Engineering* 10:423, 1997
Levy and Lee, *J Clin Invest* 109:1143-1148, 2002
Marks et al, *J. Mol. Biol.* 222:581-597, 1991
Maritano et al, *Nat Immunol.* 5:401-409, 2004
Massague et al, *Cell* 103:295-309, 2000
Meraz et al, *Cell* 84:431-442, 1996
Morrison et al, *Proc. Nat. Acad. Sci.* 81:6851, 1984
Naugler et al, *Science* 317:121-124, 2007
Nicholson et al, *Proc Natl Acad Sci USA* 97:6493-6498, 2000
Padlan et al, *Mol. Immunol.* 28:489-498, 1991
Park et al, *Gastroenterology* 119:691-698, 2000
Parkin et al, *CA Cancer J Clin* 55:74-108, 2005
Pedersen et al, *J. Mol. Biol.* 235:959-973, 1994
Rocco et al, *Annals of Oncology* 17:103-108, 2006
Takahashi-Tezuka et al, *Mol Cell Biol.* 18:4109-4117, 1998
Takaku et al, *Cancer Res.* 59:6113-6117, 1999
Uemura et al, *N Engl J Med* 345:784-789, 2001
Underhill-Day et al, *Endocrinology* 144; 3406-3414, 2003
Wang et al, *Anticancer Res.* 21:513-520, 2001
Ward et al, *Nature* 334:544, 1989
Xu et al, *Oncogene* 19:1868-1874, 2000
Yu et al, *J. Pharm Sci.* 93:48-59, 2004

---

The invention claimed is:

1. A method for the treatment of a gastrointestinal-type cancer in a subject, said method comprising administering to said subject an interleukin-11 receptor (IL-11R)-specific antagonostic antibody in an amount effective to treat said gastrointestinal-type cancer.

2. The method of claim 1 wherein the gastrointestinal-type cancer is gastric cancer or colorectal cancer.

3. The method of claim 1 wherein the amount of IL-11R-specific antibody is an amount that inhibits or reduces activation of STAT3 and/or STAT1.

4. The method of claim 1 wherein the subject is a human.

5. The method of claim 1 further comprising the administration of an anti-cancer agent.

6. The method of claim 1 further comprising radiation therapy or surgical ablation of cancer tissue.

* * * * *

SEQUENCE LISTING

```
<160> NUMBER OF SEQ ID NOS: 4

<210> SEQ ID NO 1
<211> LENGTH: 178
<212> TYPE: PRT
<213> ORGANISM: Mus musculus

<400> SEQUENCE: 1

Pro Gly Pro Pro Ala Gly Ser Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Pro Ala Ile Asp Tyr Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Ala Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
```

Arg Leu

<210> SEQ ID NO 2
<211> LENGTH: 178
<212> TYPE: PRT
<213> ORGANISM: Mus musculus

<400> SEQUENCE: 2

Pro Gly Pro Pro Ala Leu Val Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Pro Ala Ile Asp Tyr Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Cys Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu

<210> SEQ ID NO 3
<211> LENGTH: 169
<212> TYPE: PRT
<213> ORGANISM: Mus musculus

<400> SEQUENCE: 3

Val Ser Ser Asp Pro Arg Ala Asp Leu Asp Ser Ala Val Leu Leu Thr
1               5                   10                  15

Arg Ser Leu Leu Ala Asp Thr Arg Gln Leu Ala Ala Gln Met Arg Asp
            20                  25                  30

Lys Phe Pro Ala Asp Gly Asp His Ser Leu Asp Ser Leu Pro Thr Leu
        35                  40                  45

Pro Ala Ile Asp Tyr Thr Leu Gly Ser Leu Gln Leu Pro Gly Val Leu
    50                  55                  60

Thr Arg Leu Arg Val Asp Leu Met Ser Tyr Leu Arg His Val Gln Trp
65                  70                  75                  80

Leu Arg Arg Ala Gly Gly Pro Ser Leu Lys Thr Leu Glu Pro Glu Leu
                85                  90                  95

Gly Ala Leu Gln Ala Arg Leu Glu Arg Leu Leu Arg Arg Leu Gln Leu
            100                 105                 110

Leu Met Ser Arg Leu Ala Leu Pro Gln Ala Ala Pro Asp Gln Pro Val
        115                 120                 125

Ile Pro Leu Gly Pro Pro Ala Ser Ala Cys Gly Ser Ile Arg Ala Ala

```
                    130                 135                 140
His Ala Ile Leu Gly Gly Leu His Leu Thr Leu Asp Trp Ala Val Arg
145                 150                 155                 160

Gly Leu Leu Leu Leu Lys Thr Arg Leu
                165

<210> SEQ ID NO 4
<211> LENGTH: 169
<212> TYPE: PRT
<213> ORGANISM: Homo sapiens

<400> SEQUENCE: 4

Val Ser Pro Asp Pro Arg Ala Glu Leu Asp Ser Thr Val Leu Leu Thr
1               5                   10                  15

Arg Ser Leu Leu Ala Asp Thr Arg Gln Leu Ala Ala Gln Leu Arg Asp
                20                  25                  30

Lys Phe Pro Ala Asp Gly Asp His Asn Leu Asp Ser Leu Pro Thr Leu
                35                  40                  45

Pro Ala Ile Asp Tyr Ala Leu Gly Ala Leu Gln Leu Pro Gly Val Leu
            50                  55                  60

Thr Arg Leu Arg Ala Asp Leu Leu Ser Tyr Leu Arg His Val Gln Trp
65                  70                  75                  80

Leu Arg Arg Ala Gly Gly Ser Ser Leu Lys Thr Leu Glu Pro Glu Leu
                85                  90                  95

Gly Thr Leu Gln Ala Arg Leu Asp Arg Leu Leu Arg Arg Leu Gln Leu
                100                 105                 110

Leu Met Ser Arg Leu Ala Leu Pro Gln Pro Pro Asp Pro Pro Ala
            115                 120                 125

Pro Pro Leu Ala Pro Pro Ser Ser Ala Cys Gly Gly Ile Arg Ala Ala
            130                 135                 140

His Ala Ile Leu Gly Gly Leu His Leu Thr Leu Asp Trp Ala Val Arg
145                 150                 155                 160

Gly Leu Leu Leu Leu Lys Thr Arg Leu
                165
```